(12) United States Patent
Atala

(10) Patent No.: US 6,514,292 B1
(45) Date of Patent: Feb. 4, 2003

(54) CORPORAL TISSUE PENILE RECONSTRUCTION

(75) Inventor: Anthony Atala, Weston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/700,962
(22) PCT Filed: May 17, 1999
(86) PCT No.: PCT/US99/10848
§ 371 (c)(1), (2), (4) Date: Nov. 21, 2000
(87) PCT Pub. No.: WO99/59506
PCT Pub. Date: Nov. 25, 1999

Related U.S. Application Data

(60) Provisional application No. 60/086,199, filed on May 21, 1998, and provisional application No. 60/104,405, filed on Oct. 15, 1998.

(51) Int. Cl.[7] .................................................. A61F 2/26
(52) U.S. Cl. ............................... 623/23.75; 623/23.66; 623/23.72; 600/40
(58) Field of Search ........................... 623/23.66, 23.72, 623/23.75; 424/425; 600/38–41; A61F 2/26

(56) References Cited

U.S. PATENT DOCUMENTS

| | | | | |
|---|---|---|---|---|
| 4,520,821 A | * | 6/1985 | Schmidt et al. | 128/334 |
| 5,514,378 A | * | 5/1996 | Mikos et al. | 424/425 |
| 5,567,612 A | * | 10/1996 | Vacanti et al. | 435/240.23 |
| 5,624,840 A | * | 4/1997 | Naughton et al. | 435/395 |
| 5,716,404 A | * | 2/1998 | Vacanti et al. | 623/8 |
| 5,851,833 A | * | 12/1998 | Atala | 435/378 |

FOREIGN PATENT DOCUMENTS

| | | | | |
|---|---|---|---|---|
| WO | WO 99/22677 | * | 5/1999 | A61F/5/00 |
| WO | WO 99/22781 | * | 5/1999 | A61L/27/00 |

OTHER PUBLICATIONS

Atala, A., Freeman, M.R., Vacanti, J.P., Shepard, J., and Retik, A.B.: Implantation in vivo and retrieval of artificial structures consisting of rabbit and human urothelium and human bladder muscle. J. Urology, 150: 608–612, 1993.*

* cited by examiner

Primary Examiner—David H. Willse
Assistant Examiner—Javier G. Blanco
(74) Attorney, Agent, or Firm—Thomas J. Engellenner; Jasbir Sagoo; Nutter McClennen & Fish LLP

(57) ABSTRACT

A prosthetic corporal cavernosal structure (PCCS) for use in penile reconstruction, for the correction of developmental defects, for postoperative reconstruction, and for reconstructive preprosthetic surgery. The prosthetic corporal cavernosal structure (PCCS) comprises live cells seeded onto pre-formed shaped structure which may be biodegradable. The live cells may comprise smooth muscle cells such as corporal cavernosal cells, and the prosthetic corporal cavernosal structure (PCCS) for use in reconstructive surgery may be constructed of polyglycolic acid. The implant structure is applicable to use for the regeneration and reconstruction or augmentation of semirigid erectile members of the body such as the penis, and the clitoris. The prosthetic corporal cavernosal structure (PCCS) may be a composite prosthetic corporal cavernosal structure (PCCS) comprising additional anchoring and strengthening elements for anchoring or changing the structural strength of said composite prosthetic corporal cavernosal structure (PCCS).

32 Claims, 6 Drawing Sheets

CORPORAL TISSUE PENILE RECONSTRUCTION

This application claims the benefit, under 35 U.S.C. §119(e), of U.S. Provisional Application Ser. No. 60/086,199 filed on May 21, 1998, entitled "Corporal Tissue Penile Reconstruction" and U.S. Provisional Application Ser. No. 60/104,405 filed on Oct. 15, 1998, entitled "Corporal Tissue Penile Reconstruction," and International PCT Application No. PCT/US99/10848, entitled "Corporal Tissue Penile Reconstruction," filed May 17, 1999, which are hereby incorporated by reference.

BACKGROUND

1. Field of the Invention

The invention is directed to methods and materials for the treatment of penile defects by employing an implant comprising corporal cavernosal tissue grown on a support, and in particular to methods and materials useful in the reconstruction of an erectile penis.

2. Description of the Background

The penis or phallus, is the male organ of copulation and of urinary excretion, comprising a root, body, and extremity, or glans penis. The structure of the penis consists of two parallel cylindrical bodies, the corpora cavernosa and beneath them the corpus spongiosum, through which the urethra passes. The root of the penis is attached to the descending portions of the pubic bone by the crura, the latter being the extremities of the corpora cavernosa. The urethra runs along the underside of the penis then rises to open at the expanded, cone-shaped tip, the glans penis, which fits like a cap over the end of the penis. The caverna, also called the cavernae, corporum, or cavernosorum penis referred to the caverns of corpora cavernosa of the penis or the dilatable spaces within the corpora cavernosa of the penis, which fill with blood and become distended with erection. Loose skin encloses the penis and also forms the retractable foreskin or prepuce. Corporal, corporeal and corporic are terms used to describe tissues which are derived from the corpora cavernosa or which can be developed, differentiated, or altered by natural or artificial means into corpora cavernosa tissue.

A variety of congenital and acquired genitourinary tract abnormalities require surgical reconstruction and/or augmentation of the phallus. Surgeons approaching such diverse conditions as ambiguous genitalia, extrophy-epispadias complex, micropenis, aphallia, severe chordee, clubbed penis, concealed penis, double penis, webbed penis (penis palmatus), penis plastica, impotence, female to male genital reassignment, ventral hypospadias, and retracted phallus (in patients with spinal cord injury and traumatically or surgically acquired penile defects), encounter common difficulties presented by the lack of sufficient normal corporal tissue for satisfactory, functional phalloplasty (Woodhouse, C. R. J.: J. Urol., 152: 645, 1994; Atala, A et al. J. Urol., 150: 745, 1993).

Current operative modalities designed for penile reconstruction and lengthening commonly rely upon techniques developed for treatment of the epispadiac associated short phallus. Although these techniques, such as lysis of the suspensory ligament of the penis or corporal detachment from the ischiopubic rami, which were designed to free the corpora from their ligamentous attachments, have resulted in increases in the visible length of the penis, they are limited by their inherent dependence upon the presence of sufficient native corporal tissue. Many of these patients, even if potent, are dissatisfied because of limitations in penile length.

Operations designed for total or near total phalloplasty using free flap techniques may produce aesthetically acceptable results, but have been disappointing in obtaining sufficient rigidity to allow for sexual penetration. Autograft tissues, alone or in concert with synthetic penile prostheses, have been unable to satisfactorily replace the highly specialized erectile function of the penis. In addition, autologous and synthetic implants alike have resulted in numerous complications including erosion, extrusion, resorption, curving and dislodgment. It is clear that current procedures are limited because of the lack of a good substitute for normal, functional erectile tissue (Horton, C. E. and Dean, J. A.: World J. Surg., 14: 757,1990; Hage, J. J., and De Graaf, F. H.: Microsur., 14: 592, 1993).

Surgical techniques have also been inadequate in addressing the symptoms of impotence. There are many causes of impotence. Organic impotence is the loss of the ability to obtain or maintain a functional erection due to the interruption of certain physiologic processes. Causes of organic impotence include trauma such as spinal cord injury or pelvic fracture; postoperative complications such as prostatectomy, cystectomy, external sphincterotomy and abdominal perineal resection; vascular disease such as arteriosclerosis or priapism; neurologic disease such as peripheral neuropathy and multiple sclerosis; endocrinologic and metabolic disease such as diabetes, hypogonadism and renal failure; and medication such as estrogen, parasympatholytic, morphine, and heroin. The complex reflexes entailed in the mechanism of erection are also affected by physiological factors.

Phallic construction was initially attempted in the late 1930's using autogenous tissue (See e.g., Goodwin, W. E. et al., Phalloplasty. J. Urol., 68: 903, 1952). Rib cartilage has been used as a stiffener in patients with traumatic penile loss. This method involves multiple stage surgery which does not have a cosmetically satisfactory result (Frumpkin, A. P.: Am. Rev. Sov. Med., 2: 14, 1944). Silicone prostheses have become popularized in the 1970s (Bretan, P. N. Jr.: In: Genitourinary Prostheses. Montague, D. K. (ed), Philadelphia, W. B. Saunders Co., 1989; Small, M. P. et al., Urology, 5: 479, 1975) Although silicone penile prostheses are an accepted treatment modality for adults, complications such as erosion and infection remain a problem (Nukui, F. et al., Int. J. Urol., 4: 52, 1997; Kardar, A. et al., Scan. J. Urol. & Nephrol., 29: 355, 1995). Other problems reported with synthetic prostheses include extrusion through the urethra or sink of the dorsal penile shaft; lymphatic edema; irritation of the glans at the corona; slippage of the glans over the prosthesis; infection of the corpora cavernosa; crural perforation; midshaft septal perforation; and penile pain (Small, M. P. et al., Urology, 5: 479, 1975).

Although silicone penile prostheses are an accepted treatment modality for adults requiring penile reconstruction, its use has not been generally applied to the pediatric population, mainly due to the long term problems associated with these artificial devices. Thus, there is a need for biocompatible and elastic penile implants that could be used in children who require genital reconstruction.

The disadvantages of current methods have placed serious limitations on phallic reconstruction. For example, genotypic male infants born with severe pseudohermaphroditism and/or microphallus may be subjugated to gender reassignment because of the physician's inability to provide a sufficiently sized, functional neophallus. Similarly, lacking the option of receiving functional erectile tissue by transplant, the impotent patient with severe corporal fibrosis and myopathy, unresponsive to vasoactive therapeutic agents or vascular bypasses, is left with the ultimate choice of penile prosthesis placement, and is denied the future prospect of regaining normal penile erectile function.

SUMMARY OF THE INVENTION

The present invention overcomes the problems and disadvantages associated with current strategies and designs in tissue and organ reconstruction for reforming structural support members.

One embodiment of the invention is directed to an implantable prosthetic structure for use in treating a patient having an anatomical defect or erectile defect. The structural member is made from a polymeric matrix shaped in the form of a desired structural support member with dissociated corporal cavernosal cells deposited on and in the matrix such that when the matrix is implanted, a corporal cavernosal structure member is formed. The prosthetic corporal cavernosal structure has controlled biomechanical properties to provide the required structural support with erectile function in the area of the defect.

A further embodiment of the invention is directed to a method for reconstructing the penis of a patient who needs such treatment. A biocompatible synthetic or natural polymeric matrix shaped to form a structural member and adopted to fit within the corpora cavernosa or to replace the corpora cavernosa is provided. Corporal cavernosal cells are deposited on and in the polymeric matrix to form a matrix/cell construct. The matrix/cell construct is implanted into the corpora cavernosa of the patient, so that a prosthetic corporal cavernosal structure is formed in vivo with controlled biomechanical properties, thus providing the reconstructed penis with sufficient stiffness and bending strength when erect to serve as a functional organ.

While cultured cavernosum cells seeded on polymers will form corporal muscle when implanted in vivo, preferred reconstructed corporal tissue contains both endothelial and muscle cells. Therefore, this invention provides a method for developing corporal tissue in vivo by combining smooth muscle with endothelial cells (FIG. 1). Other embodiments and advantages of the invention are set forth, in part, in the description which follows and, in part, will be obvious from this description and may be learned from the practice of the invention.

DESCRIPTION OF THE INVENTION

Figure 1:
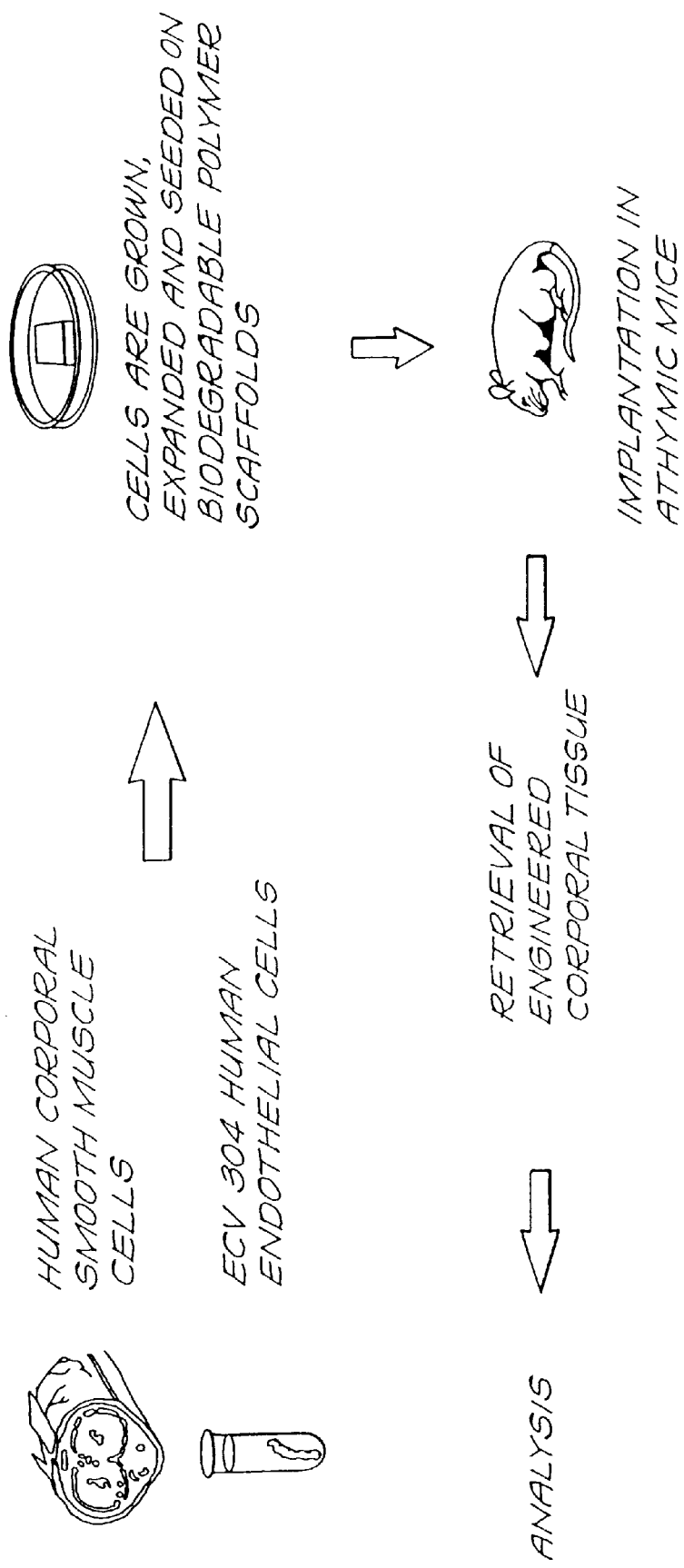
FIG. 1 shows a schematic diagram of the procedure of Example 8. Human corporal smooth muscle cells and ECV 304 human, endothelial cells are grown, expanded and seeded on biodegradable polymer scaffolds. The scaffolds are implanted in athymic mice, and retrieved at different time points for analyses.

In one broad aspect, the present invention relates to methods and materials for treating a patient having an anatomical defect of the phallus and that can be treated, at least in part; by providing an erectile structural support member to the phallus. The method may also be used to treat similar defects in the clitoris to provide needed erectile support. The requisite structural support can be provided in accordance with the present invention, by tissue engineered structural members of a predetermined shape and having controlled erectile and biomechanical properties and implanted with corporal cavernosal cells.

One advantage of the methods of the invention is that it allows a reconstructed penis to function in a manner substantially similar to native corporal tissue in regards to both anatomic and physiologic function. As it forms the bulk of the parenchyma of the corpus cavernosa, the most natural method of cavernosal reconstruction is to use corporal smooth muscle itself.

Corpora cavernosa tissue can be safely and easily obtained under local anesthesia in a percutaneous out-patient based surgical procedure (Wespes, E. et al., Eur. Urol., 18: 81, 1990). Once harvested, this tissue may be used to establish explant cultures of autologous human corporal smooth muscle cells, fibroblasts, and endothelial cells. These cells, after expansion in vitro, may be seeded onto biodegradable polyglycolic add polymer scaffolds where they can attach and multiply. Once delivered to the in vivo environment as an autograft in a reconstructive procedure, the cells may reorganize and resume their highly specialized physiologic function. The availability of harvested corporal smooth muscle cells for use in autologous cellular transplantation may be used for the treatment of impotence in accordance with this invention.

Another embodiment of the invention is directed to the treatment of diseased corporal smooth muscle cells harvested from impotent patients. Treatment may be in the form of genetic alteration. Genetic alteration may be performed using generally known techniques such as chemical-based or viral-based transfections. For example, some human corpus cavernosum smooth muscle cells are defective because of cellular overproduction of the cytokine, transforming growth factor-1 (TGF-1). The increase of TGF-1 in turn, leads to the synthesis and accumulation of excess collagen in patients with arterial insufficiency, resulting in corporal fibrosis (Moreland, R. B. et al. J. Urol., 153: 826, 1995.). While administration of prostaglandin $E_1$ ($PGE_1$) was shown to suppress this effect in vitro, the ablation of symptoms is only temporary. In an embodiment of the invention, corpora cavernosa smooth muscle cells are harvested from an impotent patient and genetically altered to reduce or eliminate TGF-1 production, or alternatively to enhance $PGE_1$ production. The cells are used for penile reconstruction. The patient may have resumption of erectile functionality once these cells are used to repopulate the diseased corporal bodies.

Another embodiment of the invention is directed to the treatment of erectile dysfunction by the preselection of a particular cell population on the basis of ultrastructural normality. The feasibility of using ultrasound to screen normal (erectile) and abnormal (non-erectile) cells has been demonstrated (Jevtich, M. et al., J. Urol., 143: 289, 1990; Persson, C. et al. J. Urol., 142: 1462, 1989). Performance of ultrastructural analysis on explant cultures from erectile dysfunctional patients, would allow the selected expansion of a population of ultrastructurally normal cells. Reintroduction of a large number of these functional cells into the corpora of these patients may be used in a restoration of erectile function. One advantage of this method is that the treatment would not involve genetic alteration. This mode of treatment may be more acceptable to some patient populations and regulatory agencies.

Another embodiment of the invention is directed to the treatment of a penile disorder by the surgical delivery of cell/polymer implants for use in genital reconstruction or as a treatment for impotence. In this method a percutaneous approach may be used wherein an injectable polymer acts as the delivery vehicle for the corporal smooth muscle cells. For example, corporal cavernosal tissue may be isolated, cultured, and expanded and mixed with an injectable matrix gel. The cell mixture is injected for percutaneous treatment of a penile disorder where a low percentage of functioning corporal smooth muscle cells are present in the native tissue.

Another embodiment of the invention is directed to the treatment of a penile disorder by reimplantation of corporal cells with an angiogenesis factor. The angiogenesis factor may be exogenous or endogenous. Exogenous angiogenesis factor may be mixed with the cell or the polymer matrix. Endogenous angiogenesis factors may be obtained by the genetic alteration of the corporal cells to express angiogenesis factors or precursors of these factors. Another method for delivering angiogenesis factors is to mix cell populations including cells which express angiogenesis factors.

One advantage of this treatment method is the ability to reverse the phenotypic modulation of corporal cells. The ability of corporal cells to maintain a functional phenotype may be dependent on a sufficient blood supply (Moreland, R. B. et al. J. Urol., 153: 826, 1995; Jevtich, M. et al., J. Urol., 143: 289, 1990; Persson, C. et al. J. Urol., 142: 1462, 1989). The transplanted cell population, much like corporal smooth muscle cells of impotent patients with chronic penile arterial insufficiency, may undergo atrophy and/or modulation to a synthetic phenotype, leading to the gradual accumulation of an extracellular matrix in the form of deposited collagen fibrils. One advantage of the method of the invention is that angiogenesis factor may result in higher oxygen tensions, would promote a greater degree of differentiation toward the contractile phenotype.

Another embodiment of the invention is directed to a method of treating a penile disorder by the use of a biodegradable polymer scaffold for corporal smooth muscle cell delivery via an anatomic, preformed structure. The delivery of corporal smooth muscle cells on such a structure, would create the possibility of a functional neo-corporal body after polymer biodegradation. Synthetic polymers also have the potential to undergo in vitro modification prior to use and could carry necessary growth factors and/or other agents which might be expected to promote cellular growth and differentiation in vivo (Langer, P, and Moses, M.: J Cell. Biochem., 45: 340, 1991).

Cells

Cells may be isolated from any tissue that comprise smooth muscle cells. One preferred tissue type for the isolation of cells is the corporal cavernosal tissue of the penis. Other tissues which may serve as a source for smooth muscle cells include cells from any muscle group in a patient. One preferred muscle group is the major nonstriated involuntary muscles from a patient body. Because the methods disclosed allow the expansion of a small initial population of muscle cells, only a small sample of tissue is required. One advantage of the ability to expand cells in vitro is that the method of treatment of the invention may be used for autologous graft and treatment of a patient even if the patient only has a limited amount of normal corporal cavernosal tissue.

Smooth muscle cells, such as corporal cavernosal cells, and preferably autologous corporal cavernosal cells can be cultured in vitro, if desired, to increase the number of such cells available for seeding on the polymeric matrix "scaffold." Culture conditions are described in the Example section of this application. The use of allogeneic cells, and more preferably autologous, corporal cavernosal cells, is preferred to prevent tissue rejection. However, if an immunological response does occur in the subject after implantation of the penile reconstruction structure, the subject may be treated with immunosuppressive agents such as, for example, cyclosporin or FK506, to reduce the likelihood of rejection of the PCCS. In certain embodiments, chimeric cells, or cells from a transgenic animal, can be seeded onto the polymeric matrix. The chimeric or transgenic cells may be genetically engineered to reduce graft rejection.

Methods for to immunorejection are known to those of skill in the art. Examples of known methods of suppressing immunorejection include the ablation or suppression (i.e., using techniques such as antisense RNA) of major and minor histocompatibility genes. For example, the expression of cell surface antigens such as class I and class II histocompatibility antigens may be suppressed. This may allow the transplanted cells to have reduced chance of rejection by the host. In addition, transfection could also be used for gene delivery. Smooth muscle cells such as corporal cavernosal cells may be induced through transfection to reduce expression of TGF-1 expression or to increase angiogenesis factor expression. Angiogenesis is important both for the erectile function of the neophallus and for the preventing the cells from differentiation into a non-erectile phenotype.

In another embodiment of the invention, corporal cavernosa cells may be transfected with specific genes prior to polymer seeding. The cell-polymer construct could carry genetic information required for the long term survival of the host or the tissue engineered neo-organ. For example, cells may be transfected to express insulin for the treatment of diabetes.

Cell cultures may be prepared with or without a cell fractionation step. A fractionation step may be useful if a high percentage of the donor cells are defective. For example, in the treatment of cancer of the penis, a sample of the corporal cavernosa tissue may be cultured and sorted to remove neoplastic cells. The remaining non-neoplastic cells may be for the reconstruction of the penis.

Cell fractionation and sorting may be performed using techniques such as fluorescent activated cell sorting with antibodies specific for a subpopulation of cells. Other criteria such as sedimentation, cell volume, electrical and radio wave transmission, and expression of EGF-1, may be employed to sort or pre-sort cells. While cell fractionation may be used, it is not necessary for the practice of the invention.

Another optional procedure in the method is cryopreservation. Cryogenic preservation may be useful, for example, to reduce the need for multiple invasive surgical procedures. The cell population may be amplified and a portion of the amplified cells may be used and another portion may be cryogenically preserved. The ability to amplify and preserve cells allows considerable flexibility in the choice of donor cells. For example, cells from a histocompatible donor, may be amplified and used in more than one recipient.

Another example of the utility of cryogenic preservation is in tissue banks. Donor cells may be cryopreserved along with histocompatibility data. Donor cells may be stored, for example, in a donor tissue bank. As tissue is needed for PCCS, cells may be selected which are most histocompatible to the patient. Patients who have a disease or undergoing conventional phalloplasty treatment may have a part of the corporal cavernosa cryogenically preserved. At a later time, if conventional treatment should prove unsuccessful, the preserved cells may be thawed for the reconstruction of the penis. Cell cyropreservation may also be useful if the patient is very young or in a medical emergency where phalloplasty must be delayed. For example, burn victims, and infants with insufficient immune systems may cyropreserve tissue for subsequent reconstruction when the patients' condition improves.

Polymeric Matrix Material

Biocompatible material and especially biodegradable material, is the preferred material for the construction of the polymeric matrix. Biocompatible refers to materials which have little or no toxic or injurious effects on biological functions. Biodegradable refers to material that can be absorbed or degraded in a patient's body. Examples of biodegradable materials include, for example, absorbable sutures. Representative materials for forming the biodegradable structure include natural or synthetic polymers, such as, for example, collagen, poly(alpha esters) such as poly (lactate acid), poly(glycolic acid), polyorthoesters and polyanhydrides and their copolymers, which degraded by hydrolysis at a controlled rate and are reabsorbed. These materials provide the maximum control of degradability, manageability, size and configuration. Preferred biodegradable polymer material include polyglycolic acid and polygalactin, developed as absorbable synthetic suture material. Polyglycolic acid and polygalactin fibers may be used as supplied by the manufacturer. Other biodegradable materials include cellulose ether, cellulose, cellulosic ester, fluorinated polyethylene, phenolicpolymer, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

In some embodiments, attachment of the cells to the polymer is enhanced by coating the polymers with compounds such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture. All polymers must meet the mechanical and biochemical parameters necessary to provide adequate support for the cells with subsequent growth and proliferation. Factors, including nutrients, growth factors, inducers of differentiation or dedifferentiation, products of secretion, immunomodulators, inhibitors of inflammation, regression factors, biologically active compounds which enhance or allow ingrowth of the lymphatic network or nerve fibers, and drugs, can be incorporated into the matrix or provided in conjunction with the matrix. Similarly, polymers containing peptides such as the attachment peptide RGD (Arg-Gly-Asp) can be synthesized for use in forming matrices.

A presently preferred biocompatible polymer is Polyglactin and polyglycolic acid. Polyglactin was developed as absorbable synthetic suture material, a 90:10 copolymer of glycolide and lactide, manufactured as Vicryl® braided absorbable sutures (Ethicon Co., Somerville, N.J.) (Craig P. H., Williams J. A., Davis K. W., et al.: A Biological Comparison of Polyglactin 910 and Polyglycolic Acid Synthetic Absorbable Sutures. Surg. 141; 1010, (1975)). Polyglactin and polyglycolic acid fibers can be used as supplied by the manufacturer. The biocompatible polymer may be shaped using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the matrix; next a solvent is used to dissolve away one of the components, resulting in pore formation. (See Mikos, U.S. Pat. No. 5,514,378, hereby incorporated by reference). In nucleation, thin films in the shape of a matrix are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a matrix structure with uniform pore sizes.

Coating refers to coating or permeating a polymeric structure with a material such as, for example, liquefied copolymers (poly-D,L-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix may be weaved, compression molded and glued together. Furthermore different polymeric materials shaped by different processes may be joined together to form a composite shape. The composite shape may be a laminar structure. For example, a polymeric matrix may be attached to one or more polymeric matrixes of the same or different composition to form a multilayer prosthetic corporal cavernosal structure. The attachment may be performed by any suitable means such as gluing with a liquid polymer, stapling, suturing, or a combination of these methods. In addition, the polymeric matrix may be formed as a solid block and shaped by laser or other standard machining techniques to its desired final form. Laser shaping refers to the process of removing materials using a laser.

The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy; with respect to toxicology by initial screening tests involving Ames assays and in vitro teratogenicity assays, and implantation studies in animals for immunogenicity, inflammation, release and degradation studies. In vitro cell attachment and viability can be assessed using scanning electron microscopy, histology, and quantitative assessment with radioisotopes.

Polymeric matrixes can be treated with additives or drugs prior to implantation (before or after the polymeric matrix is seeded with cells), e.g., to promote the formation of new tissue after implantation. Thus, for example, growth factors, angiogenesis factors, cytokines, extracellular matrix components, and other bioactive materials can be added to the polymeric matrix to promote graft healing and formation of new tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the polymeric matrix, if added cells are employed. Such additives are preferably provided in an amount sufficient to promote the formation of the neophallus, such as the formation of novel corporal cavernosal tissue. Other useful additives include antibacterial and antifungal agents to promote healing by suppression of infections.

One preferred supporting matrix is composed of crossing filaments which can allow cell survival by diffusion of nutrients across short distances once the cell support matrix is implanted.

Prosthetic Corporal Cavernosal Structure (PCCS)

The PCCS may be fabricated with controlled pore structure as described above. The size of the pores may be used to determine the cell distribution. For example, the pores on the polymeric matrix may be large to enable cell to migrate to the interior of the structure.

The polymeric matrix may be shaped into any number of desirable configurations to form a reconstructed corporal cavernosal or neophallus structure. For example, if it is desired to reconstruct the natural structure of the penis, two corporal cavernosal structures may be constructed and implanted into the patient. Alternatively, one large structure may replace both corporal cavernosal and corpus spongiosum in a patient. Preferred structures are those that roughly resemble the resultant desired corporal cavernosal or penis shape. In the cases where the PCCS is implanted to provide support for or to replace the corpora cavernosa, the PCCS may be shaped similar to the corpora cavernosa. That is, the PCCS may be shaped to form two elongated cylinders or two elongated balloons. In the case of more extensive penile reconstruction, the PCCS may be shaped to resemble an elongated rod. When designed to replace both corpora cavernosa, the PCCS may have the shape of an elongated cylinder with a kidney shaped cross section. The PCCS may be hollow or in the shape of a solid rod. If the PCCS is hollow, the hollow rod may have a space adapted for the placement of a urethra. The urethra may be natural, synthetic, or an engineered neo-urethra.

The important feature of a penile prosthesis is the ability to achieve sufficient rigidity needed to maintain its configuration. In the adult population, the prosthesis should be able to withstand certain pressure to allow coitus. Thus, it is desirable to have the cell layer of the penile prosthesis have sufficient strength to achieve erectile function. Strength in the reconstructed structure may be achieved by multiple layers of cells or the induction of a sufficiently strong layer of extracellular matrix. The shape of the polymeric matrix maybe adjusted to affect the final strength of the resultant prosthetic corporal cavernosal. For example, higher strength may be achieved by the use of a thicker and more porous layer of polymeric matrix. The thick layer will allow multiple layers of cells to form and adhere to each other.

The polymeric matrix may be sterilized using any known method before use. The method used depend on the material used in the polymeric matrix. Examples of sterilization methods include steam, dry heat, radiation, gases such as ethylene oxide, and boiling.

Seeding

The procedure for seeding the polymeric matrix is described in the Examples and further, may be performed by a number of methods such as those discussed in issued U.S. Pat. No. 5,041,138 which is herein specifically incorporated by reference.

Penile Reconstruction

Implantation and reconstruction may be performed using a number of techniques. Typically, the patient is placed in the dorsal lithotomy position and a catheter is placed in the urethra for identification purposes. A vertical midline incision is made from the base of the scrotum toward the anus and the incision is carried down to the bulbocavernosus muscle. The cavernous muscle and urethra are retracted to one side and the ischial cavernous muscle and the crus of the penis are identified. Once the crus have been identified, it is opened for a length of about 2 centimeters. Hegar dilators are used to dilate the crus of the penis proximally to the ischial tuberosity and distally for the complete extent of the corpora cavernosa. The PCCS is inserted inside the corpora. The prosthesis should fit firmly against the wall of the corpora cavernosa. Ideally, a few PCCS of different sizes should be provided. Alternatively, the surgeon may trim the PCCS to fit the patient. After one prosthesis is inserted, the same procedure may be carried out on the contralateral side. The incision in each corpora is then closed with a running suture of 3-0 chromic catgut. The remainder of the wound is closed in a routine manner. During the procedure, the PCCS are soaked in an antibiotic solution such as, for example, polymyxin-neomycin. After the insertion, the wound is irrigated with the same solution. Broad spectrum antibiotic is given and continued postoperatively. Alternative surgical procedures for implantation of PCCS will be readily apparent to those skilled in the art.

The PCCS may also be used for total penile reconstruction. Microsurgical techniques for penile reconstruction are known (see e.g., Jordan et al., J. Urol. 152:41–0414, 1994). Such techniques include the creation of a sensate neophallus initially through coaptation of the flap nerves to the genitofemoral or ilioinguinal nerves; coaptation of the local nerves of the fasciocutaneous flaps to the dorsal nerves of the penis; reconstruction using gracilis musculocutaneous flaps and ractus abdominis musculocutaneous flaps with supplementary free flaps for sensate skin coverage; faciocutaneous forearm free flap reconstruction. A neo-urethra may be fabricated along with the neophallus for a complete reconstruction. The neo-urethra may be fabricated separately and attached to the neophallus before implantation.

Alternatively, the neo-urethra may be part of the original PCCS structure which is populated with two different cell types. Thus, total phallic construction could be achieved.

PCCS could replace intracorporeal implants, thus eliminating possible complications such as erosion and infection. A similar approach could be applied to patients presenting with recurrent priapisms secondary to sickle cell anemia. Currently available managements have not proven to prevent recurrent priapism. Implantation of engineered natural prostheses composed of autologous corporal cavernosal cells would permanently eliminate the problems of blood engorgement within the corpora.

Another possible utility for PCCS would be applied toward painful genital conditions such as the Peyronie's disease. A possible therapeutic approach for these instances could be achieved by using cells transfected with genetic material. The transfected cell-polymer scaffolds forms an organ-like structure with functional expression of the delivered genes. Genes regulating inflammation and fibrosis could be delivered to the engineered penile prostheses composed of autologous corporal cavernosal cells. This gene modified prostheses would carry all the genetic information required for the functional expression in order to prevent recurrent diseases.

Human corporal smooth muscle cells have been successfully delivered to the in vivo environment, survived on biodegradable polymer scaffolds and remained differentiated. However, human endothelial cells are also present in corporal tissue. We, therefore, investigated the possibility of creating corporal tissue in vivo using human cavernosal smooth muscle cells in conjunction with human endothelial cells. In an preferred embodiment, human corporal smooth muscle and endothelial cells are seeded on biodegradable polymer scaffolds, which may be polyglycolate scaffolds, typically at concentrations of $20 \times 10^6$ cells/cm$^3$ and $10 \times 10^6$ cells/cm$^3$, respectively.

The use of endothelium has been attempted in experiments in vivo for coating grafts for vascular replacement in order to reduce the incidence of thrombosis (Herring, et al., 1978, *Surgery*, 84: 498; Machluf, et al., 1998, *Graft* 1: 31). Endothelial cells have also been used for the delivery of growth factors and cytokines in order to prevent vascular stenosis (Thompson, et al., 1988, *Science*, 241: 1349). However, to our knowledge, the use of endothelial cells as a facilitator of capillary ingrowth in composite tissue had not been attempted. Although the implantation of corporal muscle cells, alone is able to induce angiogenesis, the neovascularity is not sufficient for the creation of a normal corporal cavernosal architecture. The added implantation of endothelial cells, at the concentration usually present in normal human corporal tissue (one third endothelium), was essential for the formation of a corporal-like architecture.

We previously reported the development of a system to harvest and grow urologic cells (Atala, et al., 1993, *J. Urol.* 150:608–612; Cilento, et al., 1994, *J. Urol.*, 152: 665–670). The cells were used to create various urologic organs, including urethra, using biodegradable polymers (Atala, In Atala A, and Mooney D: Tissue Engineering. Boston, Birkhauser Press, Boston, 1997, pp 149–164; Yoo, et al., 1887, *Urology*, 51: 221; Yoo, et al., 1998, *J. Urol.*, 160: 1164). This invention provides for total phallic construction which may be achieved using tissue engineering techniques. Small penile tissue biopsies can be obtained, and urothelial, muscle and endothelial cells can be grown and expanded separately. Cells can be seeded on pre-configured biodegradable polymer scaffolds followed by the construction of a male phallus, composed of erectile tissue and a neo-urethra. In addition, genes regulating fibrosis and inflammation may be delivered to the newly formed cavernosal tissue using already established gene delivery methods (Yoo, et al., 1997, *J. Urol.*, 158:1066).

Other embodiments and advantages of the invention are set forth, in part, in the description which follows and, in part, will be obvious from this description and may be learned from practice of the invention.

EXAMPLES

Example 1

Human Corporal Smooth Muscle Cell Culture.

Explant cultures of human corpus cavernosum were derived from operative biopsies of cavernosal tissue obtained during penile prostheses implantation and processed according to previously published methods (Moreland, R. B. et al. *J. Urol.*, 153: 826, 1995). All reagents, unless otherwise specified, are standard reagents commercially available from scientific suppliers such as Gibco (Gaithersburg, Md.) or Sigma (St. Louis, Mo.). Briefly, surgical specimens were minced to small fragments of approximately 1 mm, washed in calcium and magnesium free Hank's balanced salt solution, and placed into 35 mm. cell culture wells in Dulbecco's modified Eagle's medium, containing 1 gram glucose per liter, and supplemented with 10% fetal bovine serum; 100 unit per ml penicillin, 100 $\mu$g./ml. streptomycin, 0.25 $\mu$g./ml. FUNGIZONE® (Gibco, Gaithersburg, Md.) and 2 mM. glutamine (DMEM/Supp.) The cells were cultured at 37° C., in a humidified atmosphere of 95% air and 5% $CO_2$. Over seven days in culture, smooth muscle cells were observed to migrate out from the explants. The explants were subsequently removed and the cells were allowed to grow to confluence. Cells were subcultured cell culture flasks as they reached confluence.

Cell culture medium was changed regularly every three days. Cells were subcultured into 25 centimeter diameter plastic tissue culture plates to the third passage and maintained in continuous culture for a period of 34 days.

Morphologic analyses of explant cultures of human corporal smooth muscle cells via phase contrast microscopy demonstrated smooth muscle origin in a homogeneous population of spindle shaped cells. Confluence was normally achieved 4 to 6 days after subculture and was followed by logarithmic growth of the cells in overlapping layers. Phase contrast microscopy of confluent cultures of human corpus cavernosum smooth muscle (HCPCCS) cells demonstrating "hill and valley" appearance.(Chamely-Campbell, J., Campbell, G. and Ross, R.: Physiol. Rev., 59: 1, 1979.)

During the 34-day cell culture period the cells proliferated into a multilayered "tissue-like" syncytium. On the day of polymer rod seeding, there was an average cell density of $116 \times 10^6$ viable cells per 25 cm. plate as determined by cell counting via a hemocytometer using the trypan blue exclusion method. Cellular attachment to polymer fibers was observed within 24 hours after seeding. Indirect immunofluorescent staining of cultured HCPCCS cells for alpha-smooth muscle actin confirms smooth muscle identity.

Example 2

Fabrication of the Polymer Structure.

Sheets of biodegradable, non woven polyglycolic acid polymer meshes of greater than 95% porosity were cut and fashioned into tubular rods with dimensions of 1 centimeter by 1 centimeter. A size 8 French ureteral stent was placed within each rod to assist in maintaining luminal patency. Each rod was marked at its opposing ends with sutures of 2-0 polypropylene. The average polymer fiber diameter was 15 μm. Interfiber distances varied between 0 μm. and 200 μm. Polymers were sterilized in cold ethylene oxide gas, and stored under sterile vacuum conditions until cell seeding.

Example 3

Selection of Recipients.

Young adult male athymic nu/nu (nude) mice were used as cell recipients for all experiments. The animals were housed together, allowed free access to food and water, and maintained on a cycle of about 12 hours of light and 12 hours of darkness. All animals were anesthetized with methoxyflurane by cone administration. Intramuscular injection of 1 mg. of Cefazolin served as antibiotic prophylaxis just prior to surgery. Mice were subjected to euthanasia prior to specimen removal.

Example 4

Human Corporal Smooth Muscle Cell Seeding, Implantation, and Retrieval.

Each of the 18 polymer rod biodegradable scaffolds was seeded with the human corporal smooth muscle cells of one 25 cm. plate. Cell multilayers were carefully lifted as a contiguous sheet using a Costar cell lifter and were seeded circumferentially around each polymer rod. Culture medium was removed for a period of 15 minutes to allow adequate adhesion between the polymer scaffold and the cells. Each cell/polymer scaffold was then transferred to an individual cell culture well and submerged in fresh supplemented DMEM medium. The medium was changed daily over a period of three days in culture. Phase contrast microscopic examination shows that cultured HCPCCS cells attached to biodegradable polymer scaffolds in vitro.

A total of 18 cell and polymer scaffolds were implanted subcutaneously into the flanks of athymic mice. Three seeded scaffolds were implanted per host animal. Four additional mice received one unseeded polymer scaffold and served as controls. Recipient animals were subjected to euthanasia at 7, 14, and 24 days post implantation. Cell and polymer implants were retrieved and examined grossly, histologically, immunocytochemically and by western blot analyses.

Example 5

Histological Examination of the Implants.

Implants were harvested from the flanks of athymic mice, fixed in 10% neutral buffered formalin for 6 hours and subsequently embedded in paraffin. Serial sections of 5 μm. were cut from each paraffin block. The specimens were stained with hematoxylin and eosin for conventional histology and the Masson's trichrome technique to facilitate differentiation between smooth muscle and collagen. Immunohistochemical staining for α-smooth muscle actin was performed to confirm the smooth muscle phenotype.

By seven days post implantation, histological analyses of retrieved specimens demonstrated viable smooth muscle cell multilayers oriented spatially along the surface of the polymer scaffolds. The multilayered cell population remained associated with the polymer fibers for the duration of the study. Vascular ingrowth was present in all scaffolds and increased with extended implantation times. An acute phase inflammatory response was present by 7 days which was replaced by a mild chronic foreign body reaction thereafter. Polymer fiber biodegradation was evident by 24 days. The percentage of implants containing identifiable corporal smooth muscle cells was highest at the 7 day (100%) and 14 day (100%) time points, and lowest at the 24 day (83%) time point. There was no evidence of human corporal smooth muscle in any of the control polymer implants. Masson's trichrome stain revealed viable HCPCCS cell multilayers growing along the surface of the polymer scaffold two weeks after implantation into athymic mice. Well developed smooth muscle layers accompanied by prominent vascular ingrowth were visible at 24 days post implantation.

Indirect immunofluorescent analysis using mouse monoclonal antibodies to the microfilament α-smooth muscle actin (Dako Corp., Carpinteria, Calif.) was performed on cells grown on chamber slides according to the method of Kxall et. al.(7) Briefly, cells were fixed in methanol for 5 minutes at −20° C., transferred to ice cold acetone for 5 minutes, then air dried. After rehydration in phosphate buffered saline (PBS) for 20 minutes, slides were incubated with primary monoclonal antibody to α-smooth muscle actin for one hour. Following removal of unbound antibody via three successive washes in PBS for 10 minutes, slides were incubated with fluorescein-isothiocyanate conjugated antimouse immunoglobulin for one hour. Washing was again repeated and slides were inspected by fluorescence microscopy. Negative controls were provided by the omission of primary antibody during the first incubation.

Immunocytochemical staining of retrieved, deparaffinized specimens were performed using the biotin-streptavidin method. Briefly, after quenching of endogenous peroxidase activity with 3% $H_2O_2$ in water for 5 minutes and blocking non specific binding with diluted normal horse serum in PBS for 30 minutes, slides were incubated with diluted primary antibody for one hour. Slides were then washed three times with PBS for 5 minutes and incubated for 30 minutes with diluted biotinylated anti-mouse immunoglobulins. Repeated washing was followed by incubation with the ABC reagent (Vector Laboratories, Burlingame, Calif.) for 30 minutes. After three final, 5 minute washes in PBS, sections were developed with 3,3 diaminobenzidine tetrahydrochloride for 3 minutes, counterstained with Gill's hematoxylin, and examined under light microscopy. Immunocytochemical staining of the transplanted HCPCCS cells for α-smooth muscle actin confirms smooth muscle phenotype Example 6

Western Blot Analysis.

After aspiration of all culture medium, confluent cells multilayered cultures of human corpus cavernosum smooth muscle cells grown in 25 cm diameter tissue culture plates were washed twice with ice cold PBS. Residual PBS was removed and 200 μl of 1× sodium dodecyl sulfate (SDS)-sample buffer was added to the culture dish. The lysed cells were then scraped into solution and transferred to a 1.5 ml. macro centrifuge tube. After solubilization at 100° C., debris was removed by micro centrifugation and the supernatant was transferred to a fresh tube. (8)

Polymer/cell implants and unseeded controls were harvested on days 7 and 24, frozen and stored in liquid nitrogen until use. Frozen specimens were fragmented using a mortar and pestle. Tissue fragments were washed thoroughly in ice cold PBS, then pelleted at 3000 g for 5 minutes at 4° C. Supernatant was aspirated, and three volumes of ice cold suspension buffer containing 0.1 M. sodium chloride, 0.01 M. Tris chloride (pH 7.6), 0.001 M EDTA (pH 8.0), 1 gram per ml aprotinin and 100 gram per ml phenylmethylsulfonyl fluoride were added. After addition of an equal volume of 2× SDS-sample buffer, proteins were solubilized at 100° C.

Polyacrylamide gel electrophoresis of all protein lysates (950 μg. per sample, as determined by Bio-Rad DC protein assay) was performed on a 10% separating gel, followed by electrotransfer of separated proteins onto immobilon P blotting membranes.

Immunodetection was performed according to the instruction provided by Amersham International (Buckinghamshire, England) the manufacture of the ECL detection system. Non specific binding sites were blocked in 10% (weight per volume) nonfat dried milk, 0.1% (volume per volume) Tween 20, 137 mM. sodium chloride, and 20 mM Tris base. Monoclonal antibodies for α-smooth muscle actin diluted 1:500 with blocking buffer were incubated with the membranes for 45 minutes at room temperature. After repeated washes with TBS-0.1% Tween, the membranes were incubated with anti-mouse IgG linked to horse-radish peroxidase at 1:25000 dilution with blocking buffer for 45 minutes at room temperature. The membranes were washed repeatedly in TBS-0.1% Tween, then once in TBS alone. Detection by chemiluminescence was performed using the ECL system (Amersham International, Buckinghamshire, England) by exposure of autoradiography film.

Western blot analyses of protein fractions obtained from confluent cell cultures demonstrated the presence of the 42 kDa indicating that the cultured cells is a form of α-smooth muscle actin. This result corroborates the immunocytochemical results. Western blot analysis of protein fractions obtained from HCPCCS cell-polymer implants also demonstrates the presence of the 42 kDa. protein. Thus, the HCPCCS cell-polymer implants also comprises a smooth muscle actin. In these western blot experiments, protein isolated from whole rat phallus where used as a positive control while protein isolated from vulvar epidermoid carcinoma cultured cell line A431 was used as a negative control.

Immunofluorescent cell staining with monoclonal antibodies specific for a-smooth muscle actin on cells grown in chamber slides confirmed corporal smooth muscle identity.

Example 7
Maintenance of Human Corporal Smooth Muscle Cells in vivo on Synthetic Polymers.

Histochemical staining by the Masson's trichrome technique, demonstrated a progressive qualitative increase in the amount of collagen deposition with increased implantation time. Immunocytochemical staining for a-smooth muscle actin confirmed a smooth muscle phenotype within the implants. Western blot analyses of protein fractions obtained from 7 and 24 day human corporal smooth muscle cell/polymer implants performed with monoclonal antibodies versus a-smooth muscle actin prominently demonstrated the presence of the 42 kDa. This protein was not significantly present in control polymers which were implanted without cells nor in a vulvar epidermoid carcinoma cell line (A431) used as a negative control.

Example 8
Reconstruction Using Endothelial and Muscle Cells.

ECV 304 human endothelial cells are derived from normal umbilical cord veins (Takahashi, et al., 1990, In Vitro Cell-Dev. Biol., 26:265). These cells were chosen for this study due to their unique characteristics. Unlike most endothelial cell types, ECV 304 endothelial cells do not react with anti-vWF antibodies, however, they can be identified, with several types of anti-cytokeratin antibodies (Hughes, et al., 1996, Experiment. Cell Res., 225:171). We confirmed these characteristics in culture prior to implantation, and these differences enabled us to distinguish the implanted ECV 304 cells from the host endothelial cells. In vitro, the ECV 304 cells formed an extensive capillary-like endothelial network (Riehmann, et al., 1993, J. Urol., 149:1304).

Polymers. Unwoven sheets of polyglycolic acid polymers (density 58 mg/cc) sized 1.0×1.0×0.3 cm were used as cell delivery vehicles. Nonwoven polymer meshes were composed of fibers of 15 µm in diameter with greater than 95% porosity prior to seeding. The biodegradable polymer scaffold was designed to degrade via hydrolysis in 6–8 weeks. The polymers were sterilized in ethylene oxide and stored under sterile conditions until cell delivery.

Cell Culture. Primary normal human corpus cavernosal smooth muscle cells and ECV 304 human endothelial cells (ATCC, Rockville, Md.) were used in this study. Human corporal smooth muscle tissue biopsies were obtained after informed consent during routine penile surgery. Muscle cells were isolated through established explant techniques (Moreland, et al., 1995, J. Urol., 153:826). In brief, surgical specimens were rinsed in sterile phosphate buffered saline (PBS) and minced to small fragments of approximately 1 mm in diameter. The muscle pieces were rinsed with calcium and magnesium free Hank's balanced salt solution and placed into 35 mm tissue culture plates containing Dulbecco's modified Eagle's medium (DMEM; Sigma, St.Louis, Mo.) supplemented with 10% fetal bovine serum. The cells were maintained at 37° C. in a humidified atmosphere of 95% air and 5% $CO_2$. ECV 304 human endothelial cells were plated on 100 mm tissue culture dishes containing Medium 199 (Sigma, St. Louis, Mo.) supplemented with 10% fetal bovine serum. Confluent monolayers were subcultured by treatment with 0.05% trypsin-0.53 mM EDTA 4Na (Gibco BRL, Grand Island, N.Y.) in calcium-free PBS. Both human corporal smooth muscle and endothelial cells were expanded until sufficient cell quantities were achieved. Cells were trypsinized, collected, washed and counted for seeding. Corporal smooth muscle and endothelial cells were seeded onto polyglycolic acid polymers at concentrations of $20\times10^6$ cells/$cm^3$ and $10\times10^6$ cells/$cm^3$, respectively.

Implantation. Twenty athymic mice were used as cell recipients for this study. The animals were housed together, allowed free access to food and water, and maintained on a light/dark cycle of 12 hours, respectively. All animals were anesthetized with Isoflurane by cone administration. A total of 80 polymer scaffolds (60 seeded with cells and 20 without cells) were implanted in the subcutaneous space of 20 athymic mice. Each animal had 4 implantation sites consisting of 3 polymer scaffolds seeded with muscle and endothelial cells, and a control (polymer alone). Mice were sacrificed at 1, 3, 5 and 7 days (2 each), and at 14, 21, 28 and 42 days (3 each) after implantation. The retrieved structures were analyzed grossly and histologically. Immunocylochemical and Histologic analyses. Serial sections (5 µm) of formalin fixed, paraffin embedded tissues were cut and stained with hematoxylin and eosin (H&E). Immunocytochemical analyses were performed on cultured cells grown on Lab-Tek chamber slides (Nunc, Inc., Naperville, Ill.) and the retrieved specimens using several specific antibodies. Polyclonal Anti-vWF (Dako Corp., Carpinteria, Calif.) was used to identify infiltrating host vessels. Broadly reacting monoclonal anti-pancytokeratins AE1/AE3 (Boehringer Mannheim, Indianapolis, Ind.) were used to identify ECV 304 human endothelial cells. Corporal smooth muscle fibers were labeled with monoclonal anti-alpha smooth muscle actin (Dako Corp., Carpinteria, Calif.). Immunolabeling was performed using the avidin-biotin detection system (Vector Laboratories, Burlingame, Calif.). Sections were counterstained with hematoxylin.

RESULTS

Figure 2A:
FIG. 2 shows microscopic views of a cellular structure produced according to the method of this invention. (A) ECV 304 human endothelial cells aggregated and formed an extensive capillary-like network at 27 days in culture. Phase contrast microscopy, reduced from ×100. (B) Anti-pancytokeratins stained the ECV 304 cells. Reduced from ×100. (C) Primary human corpus cavernosal smooth muscle cells stained with alpha smooth muscle actin. Reduced from ×100. (D) ECV 304 endothelial cells did not stain with polyclonal anti-vWF antibodies. Reduced from ×100.
Figure 2B:
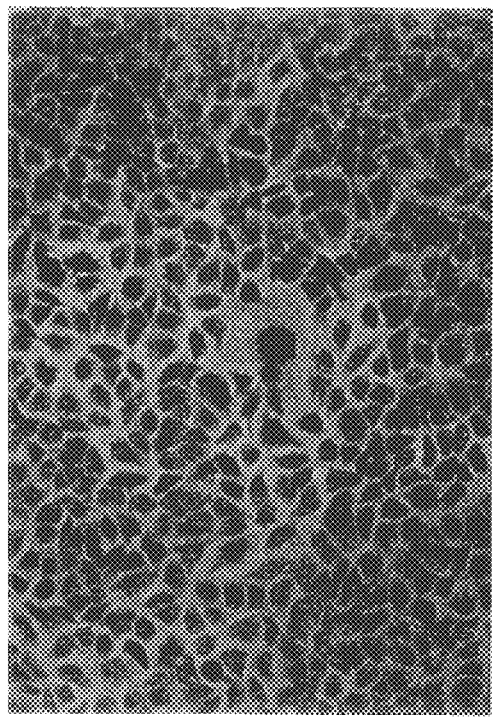
Figure 2D:
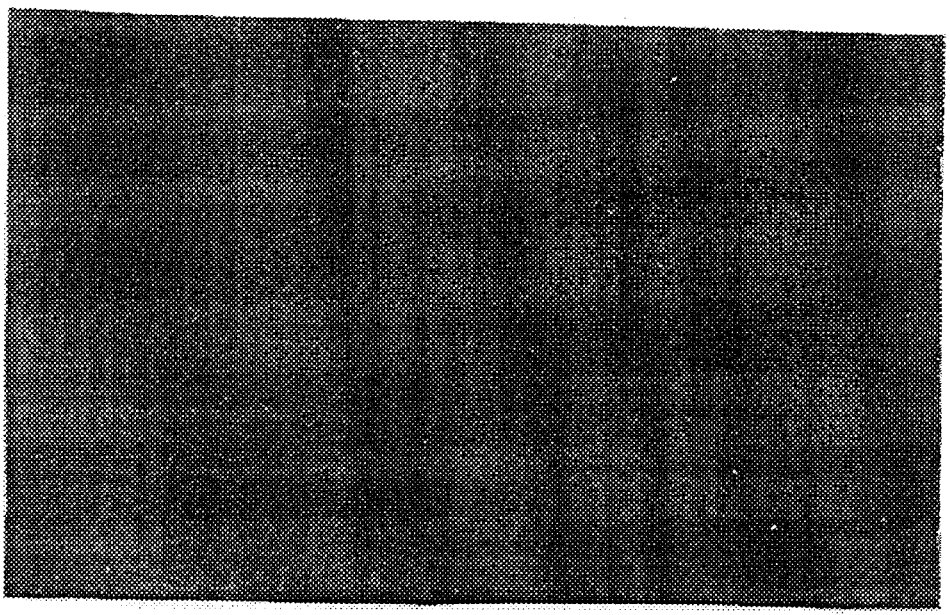
Figure 2C:
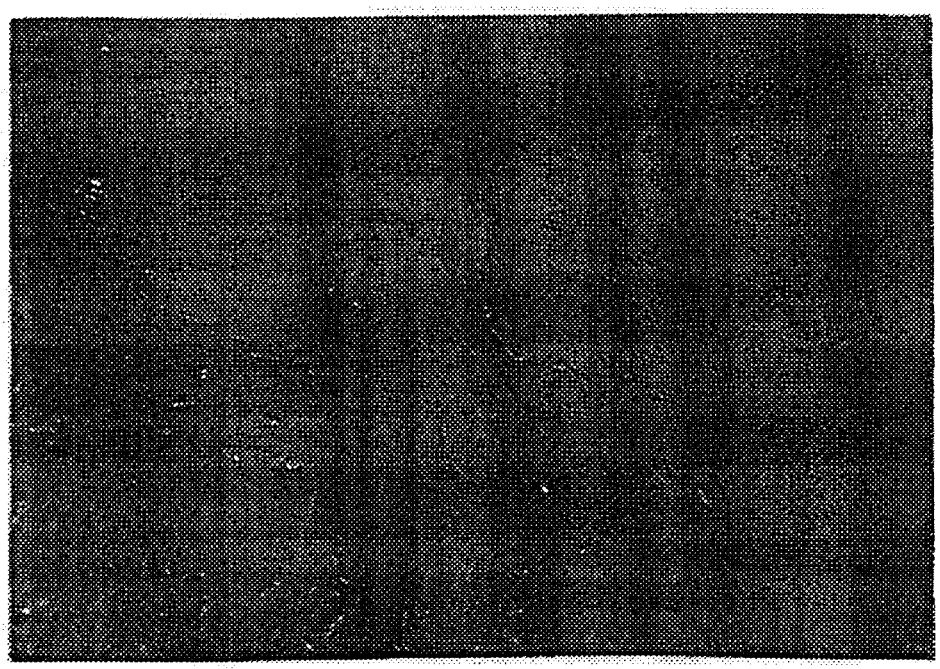

Human corpus cavernosal smooth muscle cells in culture showed homogenous populations of spindle shaped cells under phase contrast microscopy. ECV 304 human endothelial, cells were observed as cobblestone monolayers initially and progressively aggregated and formed extensive capillary-like networks by 27 days of culture (FIG. 2A). Immunocytochemical analyses of the cells in vitro were able to identify the ECV 304 human endothelial cells with anti-pancytokeratins (FIG. 2B) and the smooth muscle cells with alpha smooth muscle actin (FIG. 2C). Polyclonal anti-vWF antibodies did not stain the ECV 304 cells (FIG. 2D).

All animals survived until sacrifice without any noticeable untoward effects. At retrieval the polymer scaffolds seeded with cells had formed distinct tissue structures and maintained their pre-implantation size. The control scaffolds without cells had decreased in size with increasing time.

Figure 3:
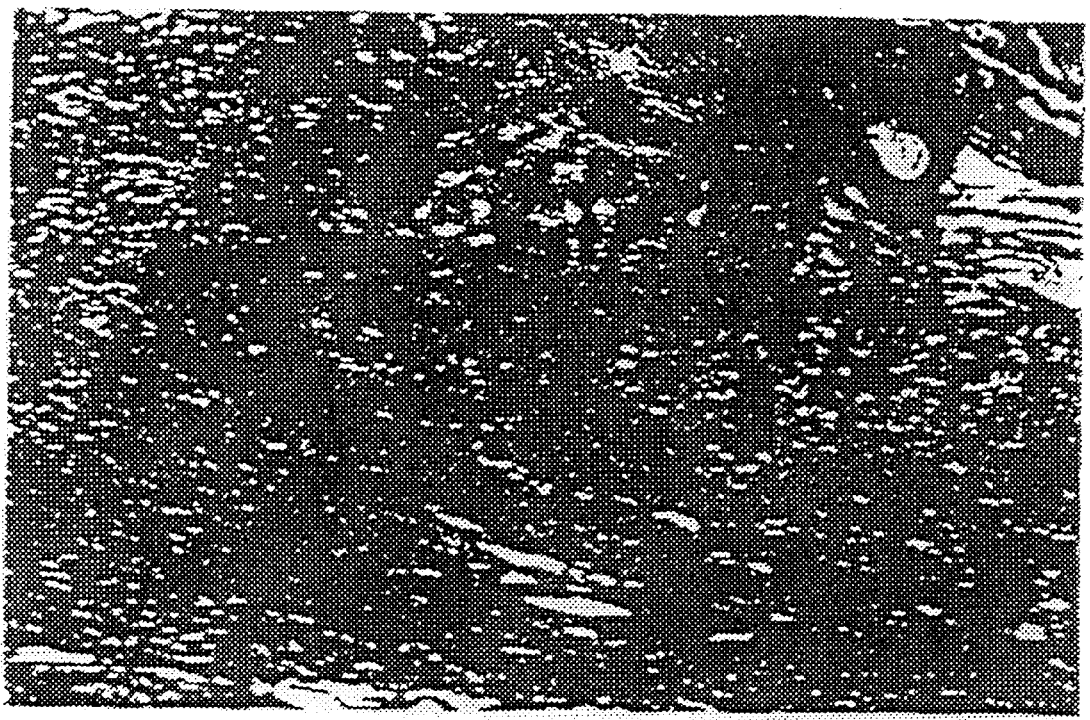
FIG. 3 shows microscopic views of a cellular structure produced according the method of this invention. Retrieved cell-polymer scaffolds at 7 days after implantation show the formation of multi-layered strips of smooth muscle adjacent to endothelium. H & E, reduced from ×250.

Histologically, the retrieved polymers seeded with corporal smooth muscle and endothelial cells showed the formation of multilayered strips of smooth muscle adjacent to endothelium 7 days after implantation (FIG. 3). The presence of penetrating native vasculature was observed. Increased smooth muscle organization and accumulation of endothelium lining the luminal structures were evident 14 days after implantation. A well organized construct, consisting of muscle and endothelial cells, was noted at 28 and 42 days after implantation. A marked degradation of the polymer fibers was observed by 28 days. There was no evidence of tissue formation in the controls (polymers without cells).

Figure 4B:
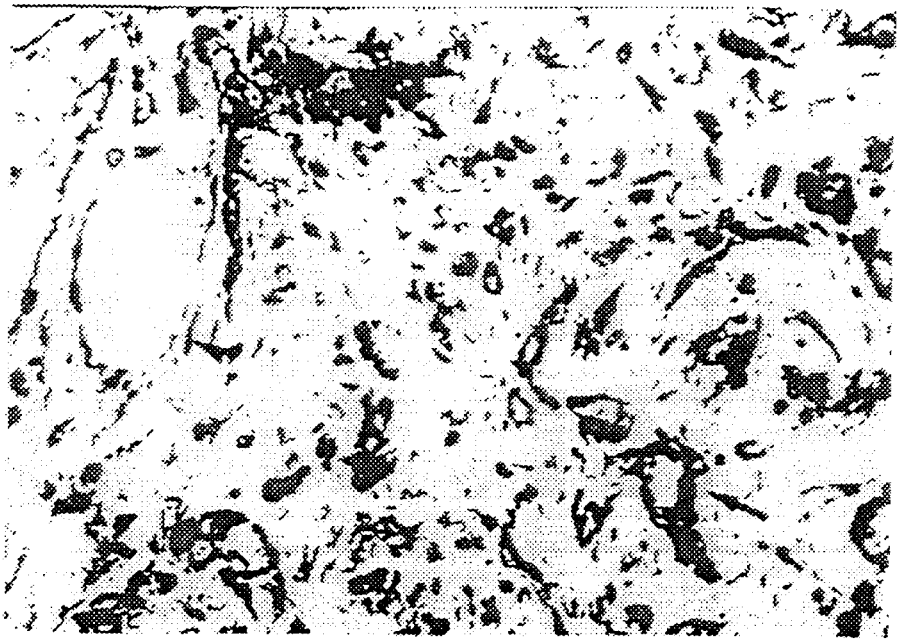
FIG. 4 shows microscopic views of a cellular structure produced according the method of this invention. (A) Immunocytochemical analyses using anti-vWF stained the native vessels 4 weeks after implantation. Neo-vessels composed of ECV 304 cells failed to stain. Reduced from ×400. Continued organization of muscle and endothelial cells is observed at 4 weeks (B) and 6 weeks (C) after implantation. ECV 304 endothelial cells and neo-vessels are stained positively, while the host vessels failed to stain with anti-pancytokeratins. Reduced from ×400. (B, 4 weeks); 200 (C, 6 weeks); ×400 (C, 4 weeks).
Figure 4A:
Figure 5:
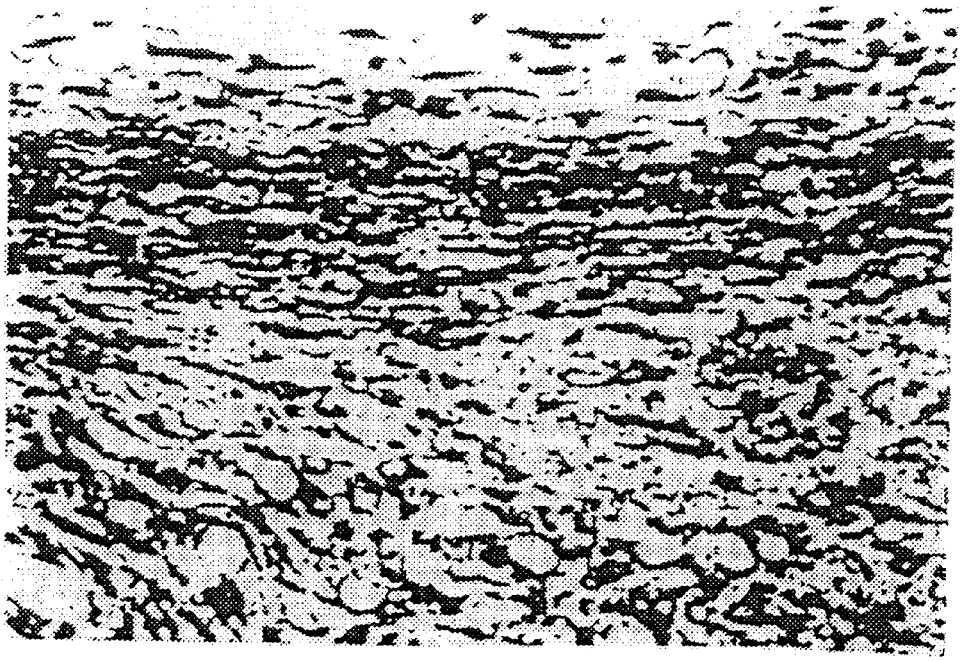
FIG. 5 shows microscopic views of a cellular structure produced according the methods of this invention. Alpha-actin antibodies identified the well organized smooth muscle tissue 6 weeks after implantation. Reduced from ×400.
Figure 4C:
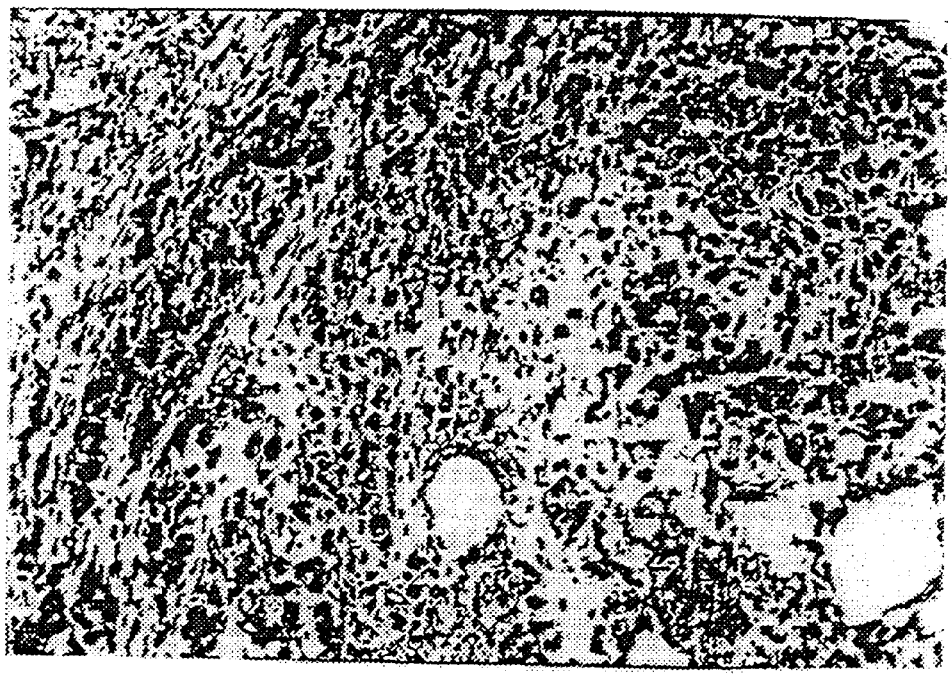

Immunocytochemical analyses using anti-vWF (identifying native vasculature) and anti-pancytokeratins (identifying ECV 304 endothelial cells) distinguished the origin of the vascular structures in each of the constructs. Anti-vWF antibodies stained the native vessels positively, but failed to stain the implanted endothelial cells and reconstituted vascular structures (FIG. 4A). In contrast, anti-pancytokeratin antibodies identified the implanted endothelial cells and the reconstituted vessels, but did not stain the native vascular structures (FIG. 4B, C). Anti-alpha actin antibodies confirmed the smooth muscle phenotype. Smooth muscle fibers were progressively organized with time (FIG. 5).

This study shows that human corporal smooth muscle cells and endothelial cells seeded on biodegradable polymer scaffolds are able to form vascularized cavernosal tissue when implanted in vivo. This is the first demonstration in tissue engineering wherein capillary formation is facilitated by the addition of endothelial cells for the formation of composite tissue. Endothelial cells are able to act in concert with the native vasculature. The creation of well vascularized autologous erectile corporal tissue consisting of smooth muscle and endothelial cells is thereby demonstrated.

This study shows that human corporal smooth muscle cells and endothelial cells seeded on biodegradable polymer scaffolds are able to form vascularized cavernosal tissue when implanted in vivo. This is the first demonstration in tissue engineering wherein capillary formation is facilitated by the addition of endothelial cells for the formation of composite tissue. Endothehal cells are able to act in concert with the native vasculature. The creation of well vascularized autologous erectile corporal tissue consisting of smooth muscle and endothelial cells is thereby demonstrated.

Other embodiments and uses of the invention will be apparent to those skilled in the art from consideration of the specification and practice of the invention disclosed herein. All U.S. Patents and other references noted herein for whatever reason are specifically incorporated by reference. The specification and examples should be considered exemplary only with the true scope and spirit of the invention indicated by the following claims.

I claim:

1. An implantable prosthetic corporal cavernosa structure for use in penile reconstruction, said structure comprising a polymeric matrix having an elongated shape and having corporal cavernosal smooth muscle cells seeded thereon, whereby upon implantation said structural member induces the growth of smooth muscle cells such that an artificial cavernosa member is formed.

2. The prosthetic corporal cavernosal structure of claim 1 wherein the polymeric matrix comprises a biocompatible material selected from the group consisting of cellulose ether, cellulose, cellulosic ester, fluorinated polyethylene, phenolic polymers, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, and copolymers or physical blends thereof.

3. The prosthetic corporal cavernosal structure of claim 1 wherein the polymeric matrix comprises a biodegradable material.

4. The prosthetic corporal cavernosal structure of claim 3 wherein the biodegradable material is a polyglycolic acid polymer.

5. The prosthetic corporal cavernosal structure of claim 1 wherein said structural member is an elongated cylinder further comprising means adapted to receive a urethra.

6. The prosthetic corporal cavernosal structure of claim 5 wherein said means adapted to receive a urethra is a longitudinal groove along its length.

7. The prosthetic corporal cavernosal structure of claim 1 wherein said structural member is a hollow cylindrical balloon with a wall thickness and a bore along its length.

8. The prosthetic corporal cavernosal structure of claim 7 wherein the hollow cylindrical balloon tube is adapted to receive a urethra along its length.

9. The prosthetic corporal cavernosa structure of claim 1 further comprising at least one end for the attachment of said implant to the descending pelvis.

10. The prosthetic corporal cavernosa structure of claim 1 wherein said structure further comprises smooth muscle cells that release prostaglandin $E_1$ ($PGE_1$).

11. The implantable prosthetic corporal cavernosa structure of claim 1 further comprising endothelial cells seeded on said polymeric matrix.

12. The implantable prosthetic corporal cavernosa structure of claim 11, wherein the endothelial cells are EC 304 human endothelial cells.

13. A method for treating a patient with a penile defect comprising the steps of:
  a) providing a polymeric matrix shaped in the form of a desired structural member;
  b) seeding said matrix by depositing dissociated smooth muscle cells on and in said matrix to form a matrix/cell construct; and
  c) implanting said matrix/cell construct within the penis of said patient wherein said construct forms a prosthetic corporal cavernosa structure having controlled biomechanical properties.

14. The method of claim 13 wherein the polymeric matrix comprises a biocompatible material selected from the group consisting of cellulose ether, cellulose, cellulosic ester, fluorinated polyethylene, phenolic polymers, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, and copolymers and physical blends thereof.

15. The method of claim 13 wherein the polymeric matrix comprises a biodegradable material.

16. The method of claim 15 wherein the biodegradable material is a polyglycolic acid polymer.

17. The method of claim 13 wherein said smooth muscle cells are corporal cavernosal cells.

18. The method of claim 17 wherein said smooth muscle cells have reduced expression of TGF-1.

19. The method of claim 18 wherein said smooth muscle cells has a elevated expression of prostaglandin $E_1$ ($PGE_1$).

20. The method of claim 13 wherein said polymetric matrix is in the shape of an hollow elongated balloon having a wall surrounding a bore extending along at least a part of its length and further comprising a means adapted to receive a urethra.

21. The method of claim 20 wherein said means adapted to receive a urethra is a longitudinal groove along its length.

22. The method of claim 13 further comprising at least one end for the attachment of said implant to the descending pelvis.

23. A method for reconstructing the penis of a patient in need of such treatment comprises the steps of
(a) providing a biocompatible synthetic or natural polymeric matrix shaped to form a structural member adapted to fit within the corpora cavernosa of said penis;
(b) depositing smooth muscle cells on and in said matrix to form a matrix/cell construct; and
(c) implanting said matrix/cell construct into the corpora cavernosa of said patient, whereby a prosthetic corporal cavernosal structure is formed in vivo, said structure having controlled biomechanical properties providing the reconstructed penis with sufficient stiffness and bending strength when erect to serve as a functional organ.

24. The method of claim 23 wherein the polymeric matrix comprises a biocompatible material selected from the group consisting of cellulose ether, cellulose, cellulosic ester, fluorinated polyethylene, phenolic polymer, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends thereof.

25. The method of claim 23 wherein the polymeric matrix comprises a biodegradable material.

26. The method of claim 25 wherein the biodegradable material is a polyglycolic acid polymer.

27. The method of claim 23 wherein said smooth muscle cells are corpora cavernosa cells.

28. The method of claim 23 wherein said structural member is an elongated cylinder further comprising means adapted to receive a urethra.

29. The method of claim 28 wherein said means adapted to receive a urethra is a longitudinal groove along its length.

30. The method of claim 28 wherein said structural member is a hollow elongated balloon with wall thickness and a bore along its length.

31. The method of claim 30 wherein the structural member is adapted to receive a urethra.

32. The method of claim 23 wherein said structure member further comprising at least one end for the attachment of said implant to the descending pelvis.

* * * * *